(12) United States Patent
Hwang et al.

(10) Patent No.: US 8,445,738 B2
(45) Date of Patent: May 21, 2013

(54) PROCESS FOR PRODUCING CUMENE

(75) Inventors: Shyh-Yuan Hwang, Needham, MA (US); Dana E. Johnson, Hopkinton, MA (US); Joseph C. Peters, Quincy, MA (US); Chung-Ming Chi, Needham, MA (US); Kevin J. Fallon, Boston, MA (US); Francis A. Demers, Holderness, NH (US)

(73) Assignee: Badger Licensing LLC, Cambridge, MA (US)

( * ) Notice: Subject to any disclaimer, the term of this patent is extended or adjusted under 35 U.S.C. 154(b) by 267 days.

(21) Appl. No.: 13/119,781

(22) PCT Filed: Sep. 23, 2009

(86) PCT No.: PCT/US2009/057941
§ 371 (c)(1),
(2), (4) Date: Mar. 18, 2011

(87) PCT Pub. No.: WO2010/042314
PCT Pub. Date: Apr. 15, 2010

(65) Prior Publication Data
US 2011/0178342 A1    Jul. 21, 2011

Related U.S. Application Data

(60) Provisional application No. 61/103,076, filed on Oct. 6, 2008.

(51) Int. Cl.
*C07C 2/86* (2006.01)
*C07C 37/08* (2006.01)

(52) U.S. Cl.
USPC .......................... 585/446; 585/469; 568/798

(58) Field of Classification Search
None
See application file for complete search history.

(56) References Cited

U.S. PATENT DOCUMENTS

| | | | |
|---|---|---|---|
| 2,410,553 A | 11/1946 | Schmerling et al. |
| 2,412,230 A | 12/1946 | Schaad et al. |
| 3,293,192 A | 12/1966 | Maher et al. |
| 3,308,069 A | 3/1967 | Wadlinger et al. |
| 3,442,795 A | 5/1969 | Kerr et al. |
| 3,449,070 A | 6/1969 | McDaniel et al. |
| 3,702,886 A | 11/1972 | Argauer et al. |
| 3,709,979 A | 1/1973 | Chu |
| 3,766,093 A | 10/1973 | Chu |
| 3,832,449 A | 8/1974 | Rosinski et al. |
| RE28,341 E | 2/1975 | Wadlinger et al. |
| 3,894,104 A | 7/1975 | Chang |
| 3,923,636 A | 12/1975 | Mead et al. |
| 3,972,983 A | 8/1976 | Ciric |
| 4,016,218 A | 4/1977 | Haag et al. |
| 4,016,245 A | 4/1977 | Plank et al. |
| 4,076,842 A | 2/1978 | Plank et al. |
| RE29,948 E | 3/1979 | Dwyer et al. |
| 4,185,040 A | 1/1980 | Ward et al. |
| 4,234,231 A | 11/1980 | Yan |
| 4,401,556 A | 8/1983 | Bezman et al. |
| 4,439,409 A | 3/1984 | Puppe et al. |
| 4,556,477 A | 12/1985 | Dwyer |
| 4,826,667 A | 5/1989 | Zones et al. |
| 4,954,325 A | 9/1990 | Rubin et al. |
| 4,992,606 A | 2/1991 | Kushnerick et al. |
| 5,015,786 A | 5/1991 | Araki et al. |
| 5,017,729 A | 5/1991 | Fukuhara et al. |
| 5,073,653 A | 12/1991 | Butler |
| 5,081,321 A | 1/1992 | Fukuhara et al. |
| 5,160,497 A | 11/1992 | Juguin et al. |
| 5,236,575 A | 8/1993 | Bennett et al. |
| 5,250,277 A | 10/1993 | Kresge et al. |
| 5,362,697 A | 11/1994 | Fung et al. |
| 5,371,310 A * | 12/1994 | Bennett et al. ............... 585/467 |
| 5,453,554 A * | 9/1995 | Cheng et al. .................. 585/467 |
| 6,077,498 A | 6/2000 | Cabanas et al. |
| 6,512,153 B1 | 1/2003 | Cappellazzo et al. |
| 6,756,030 B1 | 6/2004 | Rohde et al. |
| 6,841,704 B2 | 1/2005 | Sakuth et al. |
| 6,888,035 B2 | 5/2005 | Fallon et al. |
| 6,909,026 B2 * | 6/2005 | Dandekar et al. ............. 585/467 |
| 7,524,788 B2 | 4/2009 | Girotti et al. |
| 2008/0154080 A1* | 6/2008 | Kalyanoraman et al. ...... 585/449 |
| 2008/0194890 A1* | 8/2008 | Brown ........................... 585/16 |

FOREIGN PATENT DOCUMENTS

| | | |
|---|---|---|
| EP | 0293032 B1 | 7/1993 |
| EP | 1069099 B1 | 3/2005 |
| EP | 0371738 A2 | 11/2009 |
| EP | 2123622 A1 | 11/2009 |
| WO | 97/17290 A1 | 5/1997 |
| WO | 2008/102664 A1 | 8/2008 |
| WO | 2010/042315 A2 | 4/2010 |

OTHER PUBLICATIONS

International Search Report and Written Opinion of the International Searching Authority mailed on Mar. 30, 2010 in a corresponding application No. PCT/US2009/057941.

* cited by examiner

*Primary Examiner* — Brian J Davis
(74) *Attorney, Agent, or Firm* — Roberts Mlotkowski Safran & Cole, P.C.

(57) ABSTRACT

A process is described for producing cumene comprising contacting a feed stream comprising benzene and a further feed stream comprising isopropanol or a mixture of isopropanol and propylene in the presence of an alkylation catalyst comprising at least a molecular sieve of the MCM-22, family in an alkylation zone under alkylation conditions of at least partial liquid phase and with a water concentration in the liquid phase of at least 50 ppm to react at least part of said isopropanol and benzene to produce an effluent stream containing cumene.

22 Claims, 8 Drawing Sheets

PROCESS FOR PRODUCING CUMENE

CROSS-REFERENCE TO RELATED APPLICATIONS

This application is a national stage entry of PCT/US2009/057941 filed Sep. 23, 2009 claiming priority to U.S. Provisional application 61/103,076 filed Oct. 6, 2008.

FIELD

This invention relates to a process for producing cumene and particularly, but not exclusively, to an integrated process for producing cumene and for converting the cumene to phenol.

BACKGROUND

Cumene is an important intermediate in the chemical and polymer industries, with global cumene production in 2006, being about twelve million metric tons and with global demand of cumene being expected to grow by more than 4% per year during 2006-2011.

The majority of all cumene manufactured in the world today is used for the production of phenol. The demand for phenol for the manufacture of Bisphenol-A and subsequently polycarbonates is accelerating, owing to the broadening applications of polycarbonates in the electronic, healthcare, and automobile industries.

Cumene is typically produced commercially by reacting benzene and propylene in complete liquid phase or mixed gas-liquid phase conditions in the presence of acid catalysts. Benzene feed in stoichiometric excess relative to the propylene feed is typically fed to the reactor to control or minimize the oligomerization of the propylene which subsequently causes coking and deactivation of the catalyst. Older processes based on solid phosphoric acid typically employ a benzene to propylene feed ratio of about 8:1, molar. The high benzene to propylene feed ratio employed in these processes is also needed to limit the production of polyisopropylbenzenes, mainly diisopropylbenzenes and triisopropylbenzenes, as the polyisopropylbenzenes produced over solid phosphoric acid (SPA) catalysts cannot be converted to cumene effectively and have to be used as gasoline blending stock and regarded as a process yield loss. The high benzene to propylene feed ratio also results in large amounts of unconverted benzene in the reactor effluent that needs to be recovered by distillation and recycled back to the reactor. Both of these factors make SPA processes uneconomical.

Several processes based on aluminum chloride catalysts, developed in the 1980s, have been able to reduce the feed benzene to propylene ratio to about 3:1, molar, thus reducing the capital and operating costs related to the recovery and recycle of excess benzene, and thus improved the process economics somewhat. Although more polyisopropylbenzenes are produced in the alkylation section of the aluminum chloride processes due to the lower benzene to propylene ratios, the polyisopropylbenzenes produced in these processes can be effectively transalkylated with benzene to produce additional cumene, and the overall process yield is improved significantly over those based on SPA catalysts. However, the introduction of aluminum chloride as catalyst into the cumene plant brings with it a host of environmental, plant maintenance, and plant and personnel safety issues due to the highly corrosive nature of the catalyst. As a result, only a few cumene plants based on the aluminum chloride processes have been built.

The introduction of zeolite catalysts based cumene technologies in the 1990s has revolutionized the cumene manufacturing industry. Zeolite catalysts are non-corrosive and environmentally benign. The use of zeolite catalysts thus eliminates the environmental, maintenance, and safety concerns related to the aluminum chloride catalysts. The zeolite based processes are able to produce cumene at higher product purity and process yield than those based on solid phosphoric acid. Most zeolite based technologies are able to effect alkylation at mild conditions and with feed benzene to propylene ratios between 6:1, and 3:1 molar, somewhat lower than those employed in processes based on solid phosphoric acid, while limiting propylene oligomerization and catalyst coking to achieve a catalyst cycle length of one to two years. More advanced zeolite based technology, such as the Mobil/Badger cumene technology licensed by Badger Licensing, are able to operate at extremely low benzene to propylene ratio of 2:1 molar or lower while achieving catalyst cycle lengths of five years or more. Although more polyisopropylbenzenes are produced at low benzene to propylene ratios, they can be very efficiently transalkylated with benzene to produce additional cumene, and their effect on overall process performance is negligible. Moreover, the significant reduction in the amount of unconverted benzene that has to be recovered by distillation and recycled to the reactor results in significant reductions in both capital investment and operating costs of the cumene plant.

The rapid growth of cumene, phenol and Bisphenol-A production, however, has caused some concerns related to the imbalance of the acetone byproduct produced from the phenol plant. Acetone and phenol are produced at an approximately 1:1, molar ratio from cumene, but are used at an approximately 1:2, molar ratio in the downstream Bisphenol-A production process. The excess acetone that is not used in the production of Bisphenol-A has caused some concern from phenol producers in that it may create a supply-demand imbalance and disrupt the economics of the phenol production business.

In addition, conventional phenol production is based on the use of propylene feedstock and the need to locate phenol plants near a source of propylene has become an important issue with producers. In today's olefins market, there is also a supply-demand imbalance in the supply of propylene produced from conventional sources such as ethylene plants due to the availability of feedstock that generally favor the production of propylene. This imbalance has forced phenol producers to build their plants closer to feedstock supplies rather than to product outlets.

Numerous research efforts have been directed at solving the acetone imbalance and propylene issues described above by recycling the excess acetone produced in the phenol plant to produce cumene. For example, U.S. Pat. No. 2,410,553, teaches an alkylation process in which benzene is reacted with acetone to form cumene in the presence of hydrogen and a zinc chloride catalyst. In addition, U.S. Pat. No. 2,412,230, teaches the production of cumene from benzene and isopropanol in the presence of a pyrophosphate of a metal selected from Group IB in the periodic table.

U.S. Pat. No. 5,015,786, teaches a process for preparing phenol, comprising the steps of: (a) alkylating benzene with isopropanol using a zeolite catalyst under liquid phase conditions to synthesize cumene, (b) oxidizing the cumene from step (a) with molecular oxygen into cumene hydroperoxide, (c) subjecting cumene hydroperoxide to acid cleavage to synthesize phenol and acetone, and (d) hydrogenating the acetone from step (c) with hydrogen gas under liquid phase conditions into isopropanol which is recycled to step (a).

U.S. Pat. No. 5,017,729, discloses a process for preparing phenol, comprising the steps of: (a) reacting benzene with propylene in the presence of an aluminum chloride complex to synthesize cumene, (b) oxidizing the cumene of step (a) with molecular oxygen to cumene hydroperoxide, (c) acid cleaving cumene hydroperoxide into phenol and acetone with an acidic compound, (d) hydrogenating the acetone of step (c) with hydrogen gas into isopropanol in the presence of a hydrogenation catalyst, (e) dehydrating the isopropanol of step (d) into propylene in the presence of an acidic compound, and (f) recycling the propylene of step (e) in a liquid state to step (a).

U.S. Pat. No. 5,160,497, discloses a process for producing phenol, comprising the following successive steps: (1) benzene is reacted in an alkylation step with a feedstock comprising propylene and isopropanol in the presence of dealuminized Y zeolite with an $SiO_2/Al_2O_3$, molar ratio ranging from 8, to 70, to obtain a product which is fractionated to recover three fractions containing unconverted benzene, cumene, and polyisopropylbenzenes, respectively, (2) at least part of said polyisopropylbenzenes fraction is reacted with benzene in a transalkylation step by contacting a dealuminized Y zeolite with an $SiO_2/Al_2O_3$ molar ratio ranging from 8, to 70, and cumene is collected, (3) the cumene obtained from steps (1) and (2) is oxidized with air to obtain cumene hydroperoxide which is cleaved with an acid to obtain a mixture of phenol and acetone, which mixture is then fractionated in order to separately collect phenol and acetone, and (4) the acetone obtained at the end of step (3) is at least partly hydrogenated into isopropanol that is then at least partly recycled directly to step (1).

U.S. Pat. No. 6,841,704, discloses a method for the preparation of cumene comprising reacting isopropanol or a mixture of isopropanol and propylene with benzene in presence of a beta zeolite catalyst having a $SiO_2/Al_2O_3$ molar ratio greater than 10:1,, wherein the acidity of the catalyst is modified by surface addition of water, and wherein the isopropanol used is obtained by hydrogenation of acetone in at least two process stages.

EP 1,069,099, discloses a process in which benzene is alkylated with isopropanol or a mixture of isopropanol and propylene, under pressure and temperature conditions corresponding to complete gas phase of the mixture presence in the reaction section and in the presence of a catalyst comprising beta zeolite and an inorganic ligand.

U.S. Pat. No. 6,512,153, discloses a process in which benzene is reacted with isopropanol, alone or mixed with propylene, in the presence of a zeolite catalyst and under mixed gas-liquid phase, or complete liquid phase, at such temperature and pressure that the concentration of water in the reaction liquid phase is not higher than 8,000, ppm. The patent shows that the beta catalyst tested had adequate stability when the moisture level in the reaction liquid was maintained below 8,000, ppm. However, the catalyst deactivated significantly when the moisture content in reaction liquid exceeded 8,000, ppm.

Since the alkylation of isopropanol with benzene produces one mole of water for every mole of isopropanol consumed during the reaction, the restriction of 8,000, ppm water in the reaction liquid described in U.S. Pat. No. 6,512,153 poses a significant limit to the design of the reaction system. Such a 8,000, ppm restriction will require a very efficient removal of water within the reaction system and would require large process equipment, such as pumps, heat exchangers and decanter, and high energy consumption, resulting in high capital and operating costs and rendering such process uneconomical.

The 8,000, ppm limitation described in U.S. Pat. No. 6,512, 153, also significantly limits the integration of phenol and cumene production, since it requires that the isopropanol feed to the alkylation reactor is substantially dry. In contrast, the crude acetone produced in a conventional phenol plant (in which cumene is oxidized with molecular oxygen to cumene hydroperoxide and then cleaved to acetone and phenol) typically contains 5-10, wt % of water. Hence this large amount of water will need to be removed, either before or after the acetone is converted to isopropanol, before the isopropanol can be fed to the isopropanol alkylation reactor. This is particularly crucial for optimizing an alkylation process in which low benzene to (propylene+isopropanol) ratio is desired, because in such a case, isopropanol will constitute a major fraction of the feedstock to the alkylation reactor and the 5-10% moisture that comes with isopropanol will make the moisture content in the reactor high, even before additional moisture is produced in the alkylation reaction. Since water is difficult to remove from acetone and isopropanol, reducing the water level in acetone and isopropanol involves significant capital investment and utility consumption. If the 8,000, ppm limit on water content in the alkylation reaction liquid can be expanded substantially or removed, significant savings in capital and utility costs can be realized In accordance with the present invention, it has now been found that when an MCM-22, family molecular sieve is employed as the alkylation catalyst, benzene can be alkylated with isopropanol or a mixture of isopropanol and propylene in the presence of high levels of water in the feedstock without significant adverse affect on catalyst stability.

SUMMARY

In one aspect, the invention resides in a process for producing cumene comprising contacting a feed stream comprising benzene and a further feed stream comprising isopropanol or a mixture of isopropanol and propylene in the presence of an alkylation catalyst comprising at least a molecular sieve of the MCM-22 family in an alkylation zone under alkylation conditions of at least partial liquid phase and with a water concentration in the liquid phase of at least 50, ppm to react at least part of said isopropanol and benzene to produce an effluent stream containing cumene.

Conveniently, the concentration of water in the liquid phase is at least 100, ppm, such as at least 500, ppm, for example at least 1,000, ppm. Generally, the upper limit on the concentration of water in the liquid phase is 40,000, ppm. In one embodiment, the concentration of water in the liquid phase ranges from between 8,500, and 40,000, ppm, such as between 10,000, and 20,000, ppm.

Conveniently, said alkylation conditions comprise a temperature of about 20° C. to about 350° C., a pressure of about 100, kPa to about 20,000, kPa, and a molar ratio of benzene to $C_3$, alkylating agent (isopropanol plus any propylene) fed to said alkylation zone of about 0.1:1, to about 100:1.

In one embodiment, the molar ratio of benzene to $C_3$, alkylating agent (isopropanol plus any propylene) fed to said alkylation zone ranges from 0.3:1, to 10:1,, such as from 0.5:1, to 5:1,, for example from 1:1, to 3:1.

In one embodiment, the temperature ranges from 100, to 300° C., such as from 150, to 280° C.

Conveniently, said further feed stream comprises isopropanol or a mixture of isopropanol and propylene wherein the isopropanol to propylene molar ratio ranges from 99.9:0.1, and 0.1:99.9.

Conveniently, the process further comprises recycling at least part of said effluent stream to said alkylation zone. In one embodiment, the process further comprises cooling the effluent stream, separating said effluent stream into a water-rich aqueous stream and an aromatic stream composed mainly of cumene and unreacted benzene; and recycling at least part of said aromatic stream to the alkylation zone.

In a further aspect, the invention resides in an integrated process for producing cumene and phenol, the process comprising:

(a) alkylating benzene with a $C_3$, alkylating agent in an alkylation zone in the presence of an alkylation catalyst comprising at least a molecular sieve of the MCM-22, family to produce an alkylation effluent stream containing cumene, the reaction being carried out under complete or partial liquid phase and with a water concentration in the liquid phase of at least 50, ppm;

(b) oxidizing at least part of the cumene in step (a) to form cumene hydroperoxide;

(c) cleaving at least part of the cumene hydroperoxide in step (b) to form a cleavage effluent stream containing phenol and acetone;

(d) separating at least part of the acetone from the cleavage effluent stream in step (c);

(e) hydrogenating at least part of the acetone from step (d) to form isopropanol; and (f) recycling at least part of the isopropanol in step (e) to said alkylating step (a).

DETAILED DESCRIPTION OF THE EMBODIMENTS

Figure 1:
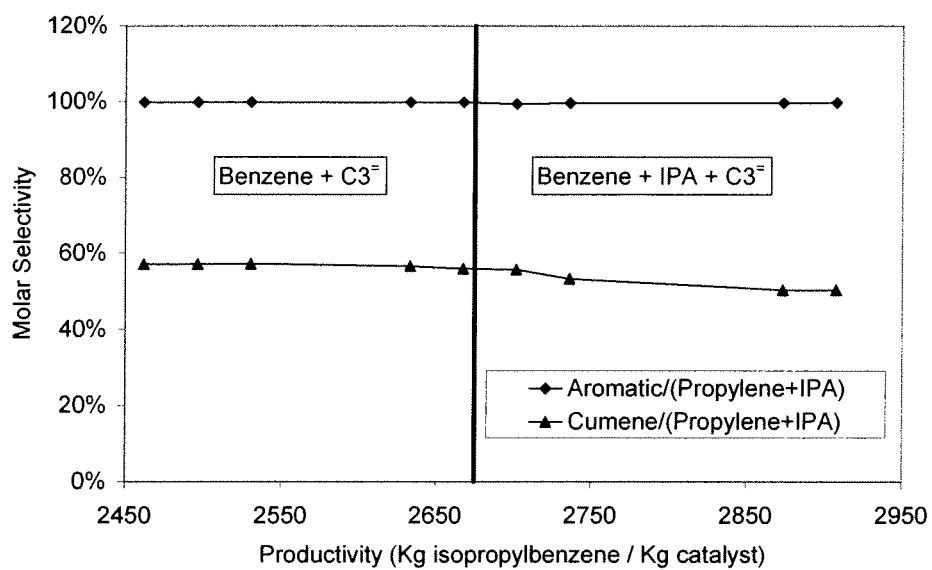
FIGS. 1 to 16 are graphs plotting aromatics selectivity and cumene selectivity against cumene productivity per gram of catalyst for the processes of Examples 1, to 16, respectively.

Described herein is a process for producing cumene by the alkylation of benzene with isopropanol or a mixture of isopropanol and propylene in the presence of an alkylation catalyst in an alkylation zone. Typically the molar ratio of benzene to the $C_3$, alkylating agent (isopropanol plus propylene) is maintained within the range of about 0.1:1, to about 100:1,, typically from 0.3:1, to 10:1,, such as from 0.5:1, to 5:1,, for example from 1:1, to 3:1. Where the $C_3$, alkylating agent comprises a mixture of isopropanol and propylene, the isopropanol to propylene molar ratio in the mixture generally ranges from 99.9:0.1, to 0.1:99.9,, such as from 90:10, to 10:90.

The alkylation reaction is conducted at a temperature of about 20° C. to about 350° C., for example about 100° C. to about 300° C., about 150° C. to 280° C. and as a pressure of about 100, kPa to about 20,000, kPa, for example about 500, kPa to about 10,000, kPa, so that at least part of the reaction mixture is maintained in the liquid phase during the process.

The catalyst employed in the alkylation zone comprises at least one molecular sieve of the MCM-22, family. As used herein, the term "molecular sieve of the MCM-22, family" (or "material of the MCM-22, family" or "MCM-22 family material" or "MCM-22, family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001,, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22, family include those molecular sieves having an X-ray diffraction pattern including d-spacing maxima at 12.4±0.25, 6.9±0.15, 3.57±0.07, and 3.42±0.07, Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22, family include MCM-22, (described in U.S. Pat. No. 4,954,325), PSH-3, (described in U.S. Pat. No. 4,439,409), SSZ-25 (described in U.S. Pat. No. 4,826,667), ERB-1, (described in European Patent No. 0293032), ITQ-1, (described in U.S. Pat. No 6,077,498), ITQ-2, (described in International Patent Publication No. WO97/17290), MCM-36, (described in U.S. Pat. No. 5,250,277), MCM-49, (described in U.S. Pat. No. 5,236,575), MCM-56, (described in U.S. Pat. No. 5,362,697), UZM-8, (described in U.S. Pat. No. 6,756,030), and mixtures thereof.

In addition to the MCM-22, family material, the alkylation catalyst may comprise at least one medium pore molecular sieve having a Constraint Index of 2-12 (as defined in U.S. Pat. No. 4,016,218). Suitable medium pore molecular sieves include ZSM-5,, ZSM-11,, ZSM-12,, ZSM-22,, ZSM-23,, ZSM-35,, and ZSM-48. ZSM-5, is described in detail in U.S. Pat. Nos. 3,702,886, and Re. 29,948. ZSM-11, is described in detail in U.S. Pat. No. 3,709,979. ZSM-12, is described in U.S. Pat. No. 3,832,449. ZSM-22, is described in U.S. Pat. No. 4,556,477. ZSM-23, is described in U.S. Pat. No. 4,076, 842. ZSM-35, is described in U.S. Pat. No. 4,016,245. ZSM-48, is more particularly described in U.S. Pat. No. 4,234,231.

Alternatively, the alkylation catalyst may comprise one or more large pore molecular sieves having a Constraint Index less than 2, in addition to the MCM-22, family material. Suitable large pore molecular sieves include zeolite beta, zeolite Y, Ultrastable Y (USY), Dealuminized Y (Deal Y), mordenite, ZSM-3, ZSM-4,, ZSM-18,, and ZSM-20. Zeolite ZSM-14, is described in U.S. Pat. No. 3,923,636. Zeolite ZSM-20, is described in U.S. Pat. No. 3,972,983. Zeolite Beta is described in U.S. Pat. Nos. 3,308,069,, and Re. No. 28,341. Low sodium Ultrastable Y molecular sieve (USY) is described in U.S. Pat. Nos. 3,293,192, and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766, 093, and 3,894,104.

The above molecular sieves may be used as the alkylation catalyst without any binder or matrix, i.e., in so-called selfbound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1, to about 90, percent by weight and more usually, particularly, when the composite is prepared in the form of beads, in the range of about 2, to about 80, weight percent of the composite.

The alkylation reaction may be carried out batchwise or on a continuous basis. Moreover, the reaction may be carried out in a fixed or moving bed. Fixed bed operation is, however, preferred, typically with the alkylation reaction zone comprising one or a plurality of series-connected beds of alkylation catalysts.

The alkylation reaction is generally operated so as to achieve substantially complete conversion of the $C_3$, alkylating agent (isopropanol plus any propylene) and hence the effluent from the alkylation zone is composed mainly of cumene, coproduced and cofed water, unreacted benzene, and other reaction products. Part of the effluent is typically recycled to the alkylation zone in order to control the reaction temperature. It is, however, important to avoid excessive build-up of water in the alkylation reactor and hence the alkylation effluent is at least partially dewatered before the effluent is recycled. The effluent stream can be cooled, separated into a water-rich aqueous stream and a water-depleted aromatic stream comprising cumene, unreacted benzene, and other reaction products. Part of the aromatic stream is then recycled to the alkylation reaction zone.

By using a catalyst comprising at least one molecular sieve of the MCM-22, family, it is found that the present alkylation process is unusually tolerant to the presence of water in the liquid phase of the alkylation reaction zone. Thus, whereas it is normal to dry alkylation feeds so that the total water content in the liquid phase reaction medium is very low (typically well below 50 pmm), it is found that the present process can operate with water levels of at least 50, ppm, such as at least 100, ppm, for example at least 500, ppm, such as at least 1,000, ppm or even at least 5,000, ppm, without significant loss of catalyst stability. Generally, the upper limit on the concentration of water in the liquid phase is 40,000, ppm. In one embodiment, the concentration of water in the liquid phase ranges from between 8,500, and 40,000, ppm, such as between 10,000, and 20,000 ppm. Water levels within these ranges can generally be achieved by suitable control of the water content of the $C_3$, alkylating agent (with or without partial drying), the amount of alkylation effluent recycle, and/or the water content of alkylation effluent recycle.

In one embodiment, the present process for converting isopropanol to cumene forms part of an integrated process for producing phenol. In such an integrated process, the cumene produced in the present process is oxidized to form cumene hydroperoxide and the cumene hydroperoxide is cleaved to form a cleavage effluent stream containing phenol and acetone. The acetone is then separated from the cleavage effluent stream, hydrogenated to isopropanol and recycled back to the present process. Details of the cumene oxidation and cleavage steps can be found in, for example, U.S. Pat. No. 5,017,729, which is incorporated herein by reference. Details of the acetone hydrogenation to isopropanol can be found in, for example, U.S. Pat. No. 5,081,321, also incorporated herein by reference.

EXAMPLE 1

An alkylation test of benzene with isopropanol and propylene was carried out in a fixed bed reactor, made from a ¾, inch (19, cm) diameter Schedule 40, Stainless Steel 316, pipe with a total length of 34, inches (864, cm). A storage tank was used for the benzene/isopropanol mixture and another tank was used for propylene. A positive displacement pump was used for feeding the benzene/isopropanol mixture into the reactor and another positive displacement pump was used for feeding propylene into the reactor. The flow rates of the benzene/isopropanol mixture and propylene were set by pump settings and monitored by electronic weight scales. The reactor operating conditions were controlled and monitored by an automatic control system. A portion of the reactor effluent was circulated back to the reactor inlet by a centrifugal pump to control the temperature rise across the catalyst bed. The feedstock and reactor effluent were analyzed by two Hewlett Packard 5890, Series II Gas Chromatographs, one equipped with a Chrompack CP-Wax 52CB column having an inside diameter of 0.25, mm, film thickness of 0.5, μm, and length of 60, meters, and the other one equipped with an Agilent HP-PONA column having an inside diameter of 0.20 mm, film thickness of 0.5, μm, and length of 50, meters.

60, grams of an MCM-22, catalyst was loaded into the fixed bed reactor. Before the benzene/isopropanol mixture was introduced into the reactor, the feed to the reactor consisted of pure benzene and propylene and the catalyst performance was stable. The propylene feed weight hourly space velocity (WHSV) was 0.5, $hr^{-1}$, the feed benzene to propylene ratio was 1.2:1, molar, and the reactor inlet temperature was 128° C. The reactor circulation was adjusted to control the temperature rise across the catalyst bed below 20° C. As shown in FIG. 1, after the pure benzene feed was replaced with a mixture consisting of 1 wt % isopropanol and 99, wt % benzene and the reactor inlet temperature adjusted to 147° C., the Cumene/(Isopropanol+Propylene) selectivity went down slightly and stabilized at a lower level than before, due to a slight increase in the production of polyisopropylbenzenes. The Aromatics/(Isopropanol+Propylene) selectivity remained essentially unchanged throughout the test, as shown in FIG. 1. No gradual or rapid aging as shown in the examples of U.S. Pat. No. 6,512,153 was observed. The propylene conversion was 100% and the isopropanol conversion was 99%. The moisture level in the reactor was about 20, ppm with the benzene feed and about 2,100, ppm with the benzene/isopropanol mixture. The corresponding isopropanol WHSV was 0.01, and the isopropanol to propylene molar ratio in the reactor feed was 2:98.

EXAMPLE 2

30, grams of an MCM-49, catalyst was loaded into the fixed bed reactor described above. The reactor effluent was cooled to near ambient temperature and then the free water was removed in a decanter. A portion of the reactor effluent, after the free water was removed in the decanter, was circulated back to the reactor inlet by the centrifugal pump described in Example 1, to control the moisture content in the reactor.

Figure 2:
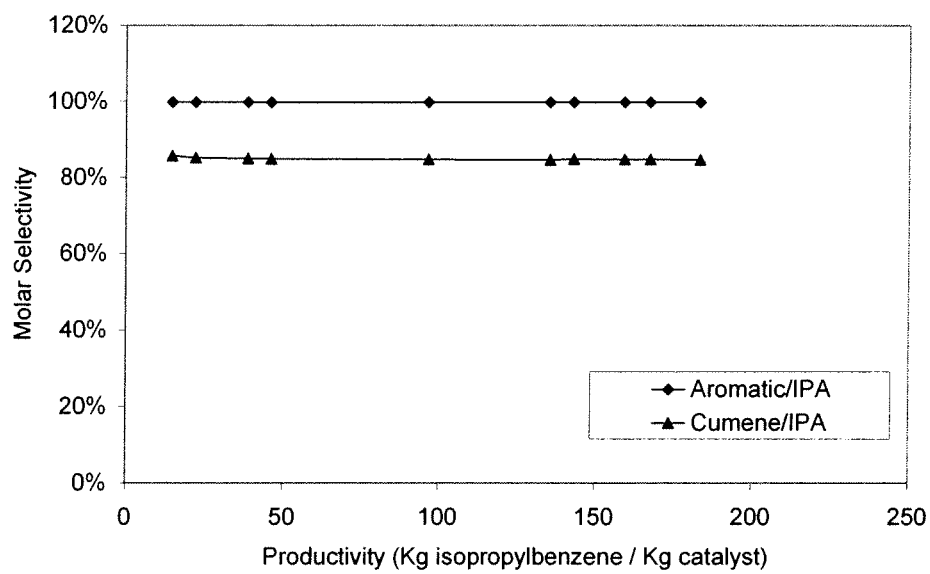

A feed comprised of 88.6, wt % benzene and 11.4, wt % isopropanol, equivalent to benzene to isopropanol molar ratio of 6:1,, was fed to the reactor at 134, grams per hour, giving an isopropanol WHSV of 0.5, $hr^{-1}$. The reactor circulation was adjusted to give a moisture content of 10,300, ppm in the reactor. The inlet temperature was 210° C., the reactor pressure was maintained at 470, psig (3342, kPa), and the reaction took place in complete liquid phase. The isopropanol conversion was 100% throughout the run. The Cumene/Isopropanol selectivity observed in this example was much higher than the Cumene/(Isopropanol+Propylene) selectivity observed in Example 1,, due to reduced polyisopropylbenzenes production at higher benzene to (Isopropanol+Propylene) ratio in this example than in the previous example. As shown in FIG. 2, the catalyst performance was stable throughout the run and no gradual or rapid aging as shown in the Examples of U.S. Pat. No. 6,512,153, was observed.

EXAMPLE 3

Figure 3:
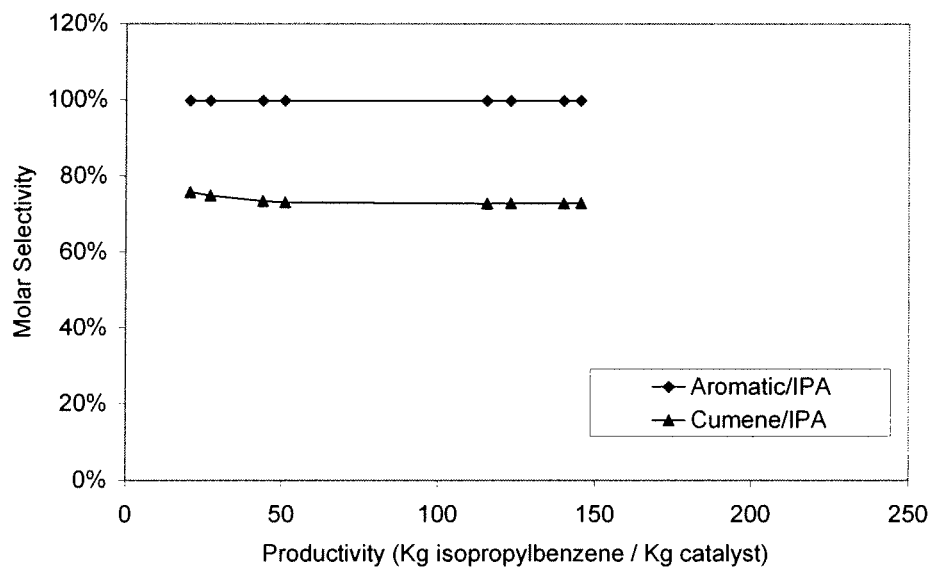

The same reactor setup and catalyst loading described in Example 2 were used in this example. A feed comprised of 79.6, wt % benzene and 20.4, wt % isopropanol, equivalent to a benzene to isopropanol molar ratio of 3:1,, was fed to the reactor at 75, grams per hour, giving an isopropanol WHSV of 0.5, $hr^{-1}$. The reactor circulation was adjusted to give a moisture content of 10,400, ppm in the reactor. The inlet temperature was 210° C., the reactor pressure was maintained at 470, psig (3342, kPa), and the reaction took place in complete liquid phase. The isopropanol conversion was 100% throughout the run. The Cumene/Isopropanol selectivity observed in this example was lower than that observed in Example 2, due to increased polyisopropylbenzenes production at lower benzene to isopropanol ratio in this example. As shown in FIG. 3, the catalyst performance was stable after the initial adjustment was made and no gradual or rapid aging as shown in the Examples of U.S. Pat. No. 6,512,153, was observed.

EXAMPLE 4

Figure 4:
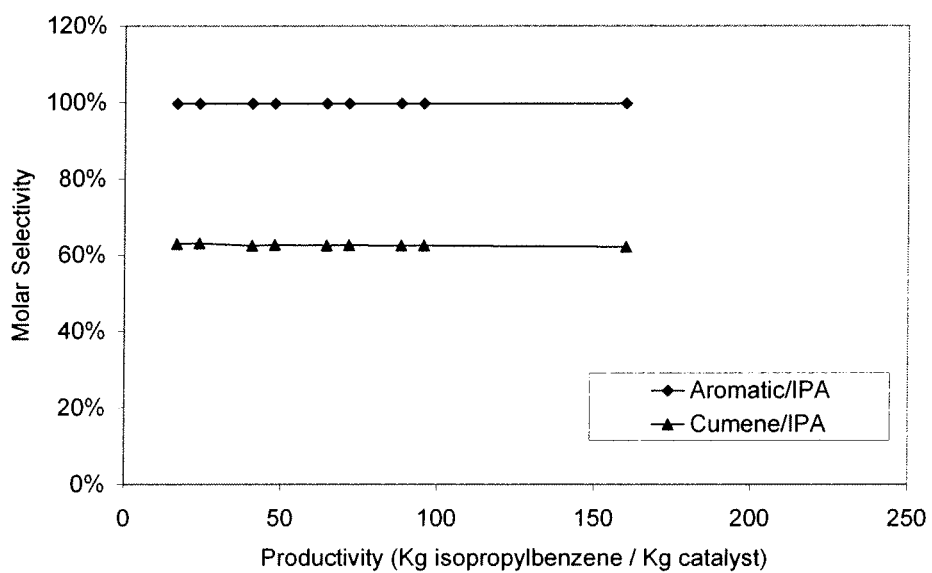

The same reactor setup and catalyst loading described in Example 2 were used in this example. A feed comprised of 72.2, wt % benzene and 27.8, wt % isopropanol, equivalent to a benzene to isopropanol molar ratio of 2:1,, was fed to the reactor at 55, grams per hour, giving an isopropanol WHSV of 0.5, $hr^{-1}$. The reactor circulation was adjusted to give a moisture content of 10,400, ppm in the reactor. The inlet temperature was 230° C., the reactor pressure was maintained at 470, psig (3342, kPa), and the reaction took place in complete liquid phase. The isopropanol conversion was 100% throughout the run. The Cumene/Isopropanol selectivity observed in this example was lower than that observed in example 3, due to increased polyisopropylbenzenes production at lower benzene to isopropanol ratio in this example. As shown in FIG. 4, the catalyst performance was stable throughout the run and no gradual or rapid aging as shown in the Examples of U.S. Pat. No. 6,512,153, was observed.

EXAMPLE 5

Figure 5:
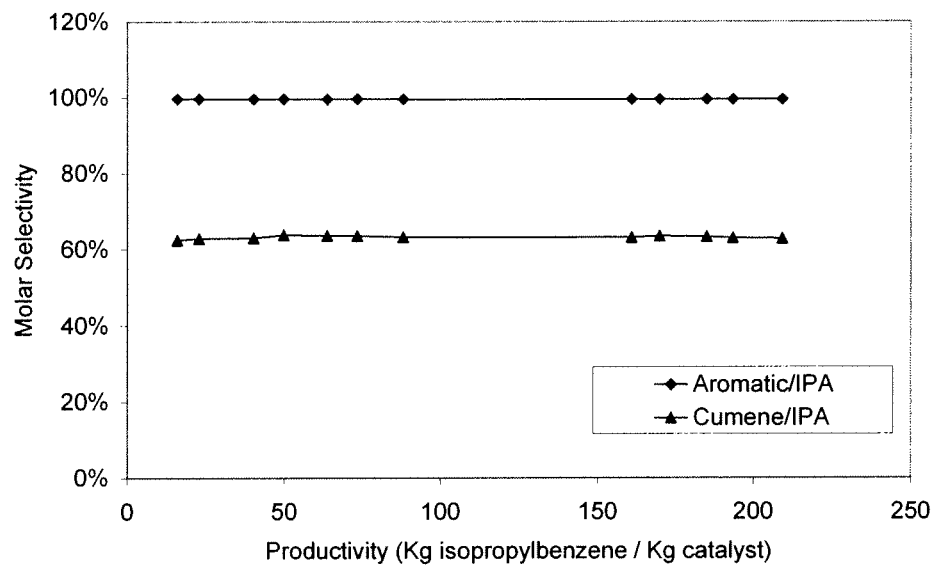

The same reactor setup and catalyst loading described in Example 2 were used in this example. A feed comprised of 72.2, wt % benzene and 27.8, wt % isopropanol, equivalent to a benzene to isopropanol molar ratio of 2:1,, was fed to the reactor at 55, grams per hour, giving an isopropanol WHSV of 0.5, $hr^{-1}$. The reactor circulation was adjusted to give a moisture content of 14,950, ppm in the reactor. The inlet temperature was 230° C., the reactor pressure was maintained at 470, psig (3342, kPa), and the reaction took place in complete liquid phase. The isopropanol conversion was 100% throughout the run. The Cumene/Isopropanol selectivity observed in this example was slightly higher than that observed in example 4,, due to slightly lower polyisopropylbenzenes production at the higher moisture content in this example. As shown in FIG. 5, the catalyst performance was stable throughout the run and no gradual or rapid aging as shown in the Examples of U.S. Pat. No. 6,512,153, was observed.

EXAMPLE 6

Figure 6:
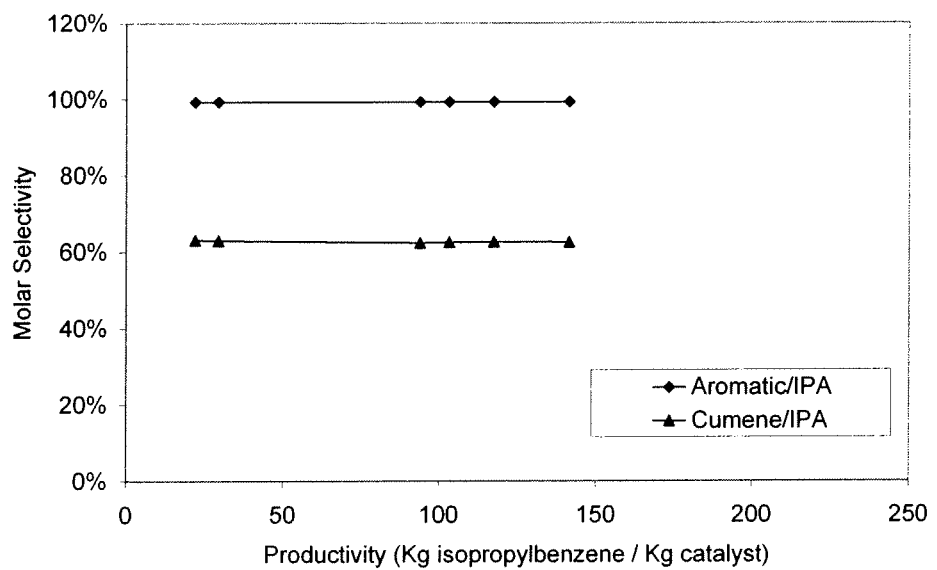

The same reactor setup and catalyst loading described in Example 2 were used in this example. A feed comprised of 72.2, wt % benzene and 27.8, wt % isopropanol, equivalent to a benzene to isopropanol molar ratio of 2:1,, was fed to the reactor at 56, grams per hour, giving an isopropanol WHSV of 0.5, $hr^{-1}$. The reactor circulation was adjusted to give a moisture content of 20,000, ppm in the reactor. The inlet temperature was 230° C., the reactor pressure was maintained at 540, psig (3824, kPa), and the reaction took place in complete liquid phase. The isopropanol conversion was 100% throughout the run. The Cumene/Isopropanol selectivity observed in this example was similar to that observed in example 5. As shown in FIG. 6, the catalyst performance was stable throughout the run and no gradual or rapid aging as shown in the Examples of U.S. Pat. No. 6,512,153, was observed.

EXAMPLE 7

Figure 7:
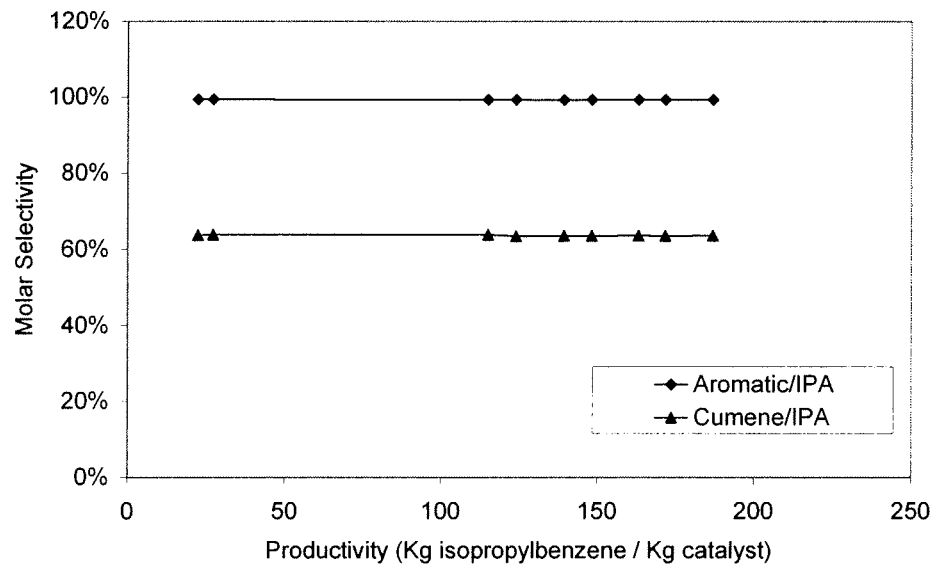

The same reactor setup and catalyst loading described in Example 2 were used in this example. A feed comprised of 72.2, wt % benzene and 27.8, wt % isopropanol, equivalent to a benzene to isopropanol molar ratio of 2:1,, was fed to the reactor at 56, grams per hour, giving an isopropanol WHSV of 0.5, $hr^{-1}$. The reactor circulation was adjusted to give a moisture content of 23,700, ppm in the reactor. The inlet temperature was 230° C., the reactor pressure was maintained at 470, psig (3342, kPa), and the reaction took place in mixed gas-liquid phase. The moisture content in the liquid phase was calculated to be 18,600, ppm. The isopropanol conversion was 100% throughout the run. The Cumene/Isopropanol selectivity observed in this example was slightly higher than that observed in example 6. As shown in FIG. 7, the catalyst performance was stable throughout the run and no aging as shown in the Examples of U.S. Pat. No. 6,512,153, was observed.

EXAMPLE 8

Figure 8:
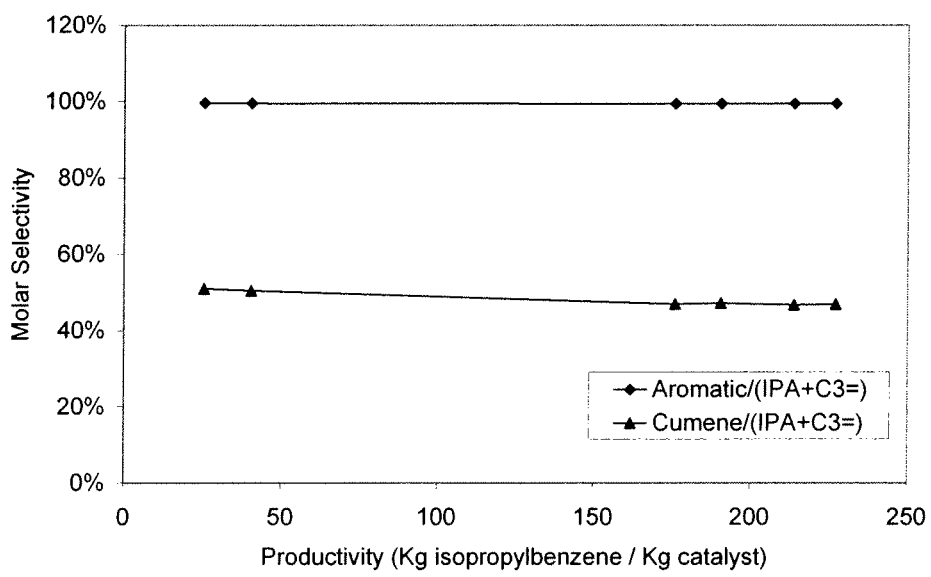

The same reactor setup and catalyst loading described in Example 2 were used in this example. A feed comprised of 72.2, wt % benzene and 27.8, wt % isopropanol, equivalent to benzene to isopropanol molar ratio of 2:1,, was fed to the reactor at 54, grams per hour, giving an isopropanol WHSV of 0.5, $hr^{-1}$. In addition, propylene was fed to the reactor at 6, grams per hour, giving a propylene WHSV of 0.2, $hr^{-1}$. The overall Benzene to (Isopropanol+Propylene) molar ratio was 1.3:1, and the isopropanol to propylene molar ratio in the reactor feed was 64:36. The reactor circulation was adjusted to give a moisture content of 8,600 ppm in the reactor. The inlet temperature was 230° C., the reactor pressure was maintained at 470, psig (3342, kPa), and the reaction took place in complete liquid phase. The propylene and isopropanol conversions were both 100% throughout the run. As shown in FIG. 8, the catalyst performance was stable after the initial change in Cumene/(Isopropanol+Propylene) selectivity due the reduction of benzene to (Isopropanol+Propylene) ratio at the beginning of the run. No gradual or rapid aging as shown in the Examples of U.S. Pat. No. 6,512,153, was observed.

EXAMPLE 9

Figure 9:
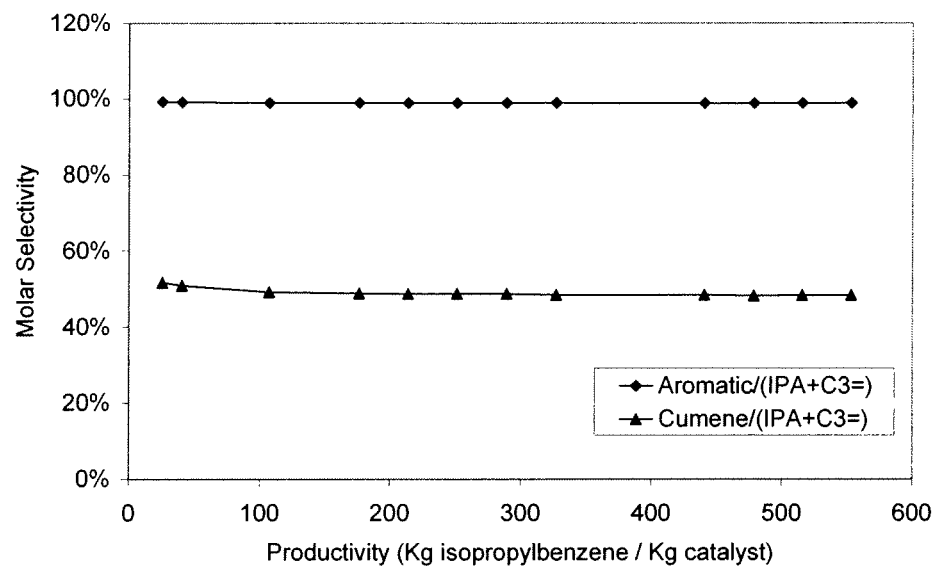

The same reactor setup and catalyst loading described in Example 2 were used in this example. A feed comprised of 72.2, wt % benzene and 27.8, wt % isopropanol, equivalent to benzene to isopropanol molar ratio of 2:1,, was fed to the reactor at 56, grams per hour, giving an isopropanol WHSV of 0.5, $hr^{-1}$. In addition, propylene was fed to the reactor at 6, grams per hour, giving a propylene WHSV of 0.2, $hr^{-1}$. The overall Benzene to (Isopropanol+Propylene) molar ratio was 1.3:1, and the isopropanol to propylene molar ratio in the reactor feed was 64:36. The reactor circulation was adjusted to give a moisture content of 19,300 ppm in the reactor. The inlet temperature was 230° C., the reactor pressure was maintained at 470, psig (3342, kPa), and the reaction took place in mixed gas-liquid phase. The moisture content in the liquid phase was calculated to be 15,800, ppm. The propylene and isopropanol conversions were both 100% throughout the run. As shown in FIG. 9, the catalyst performance was stable after the initial change in Cumene/(Isopropanol+Propylene) selectivity. No gradual or rapid aging as shown in the Examples of U.S. Pat. No. 6,512,153, was observed.

EXAMPLE 10

Figure 10:
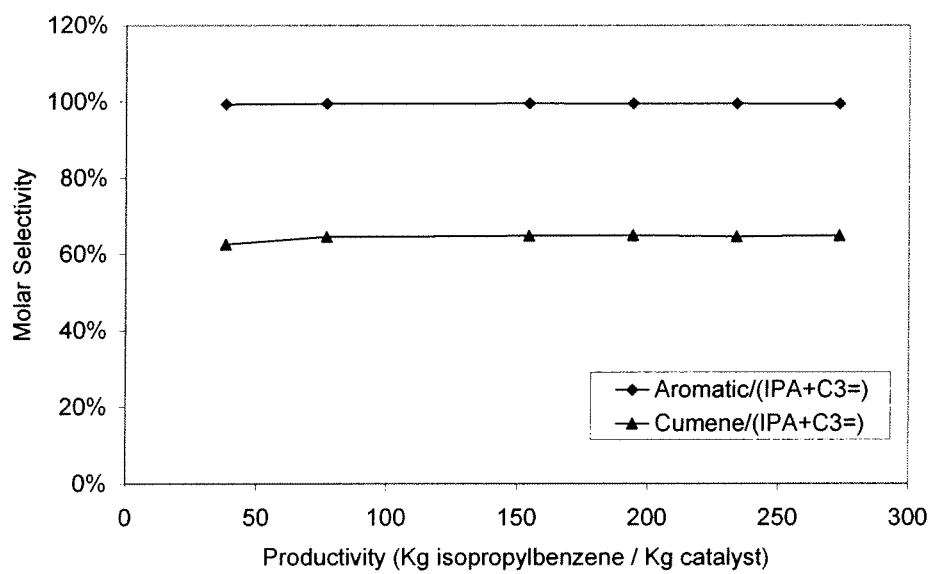

The same reactor setup and catalyst loading described in Example 2 were used in this example. A feed comprised of 87.1, wt % benzene and 12.9, wt % isopropanol, equivalent to benzene to isopropanol molar ratio of 5.2:1,, was fed to the reactor at 95, grams per hour, giving an isopropanol WHSV of 0.4, $hr^{-1}$. In addition, propylene was fed to the reactor at 9, grams per hour, giving a propylene WHSV of 0.3, $hr^{-1}$. The overall Benzene to (Isopropanol+Propylene) molar ratio was 2.5:1, and the isopropanol to propylene molar ratio in the reactor feed was 49:51. The reactor circulation was adjusted to give a moisture content of 8,500 ppm in the reactor. The inlet temperature was 230° C., the reactor pressure was maintained at 470, psig, and the reaction took place in complete liquid phase. The propylene and isopropanol conversions were both 100% throughout the run. As shown in FIG. 10, the catalyst performance was stable after the initial change in Cumene/(Isopropanol+Propylene) selectivity due the increase of benzene to (Isopropanol+Propylene) ratio at the beginning of the run. No gradual or rapid aging as shown in the Examples of U.S. Pat. No. 6,512,153, was observed.

EXAMPLE 11

Figure 11:
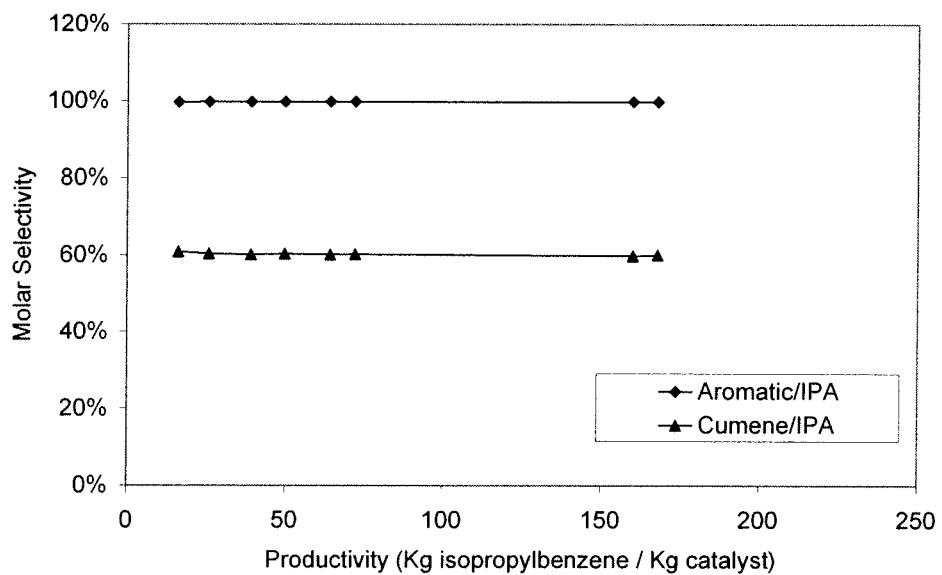

The same reactor setup and catalyst loading described in Example 2 were used in this example. A feed comprised of 72.2, wt % benzene and 27.8, wt % isopropanol, equivalent to a benzene to isopropanol molar ratio of 2:1,, was fed to the reactor at 56, grams per hour, giving an isopropanol WHSV of 0.5, $hr^{-1}$. The reactor circulation was adjusted to give a moisture content of 5,300, ppm in the reactor. The inlet temperature was 230° C., the reactor pressure was maintained at 470, psig (3342, kPa), and the reaction took place in complete liquid phase. The isopropanol conversion was 100% throughout the run. As shown in FIG. 11, the catalyst performance was stable throughout the run.

EXAMPLE 12

Figure 12:
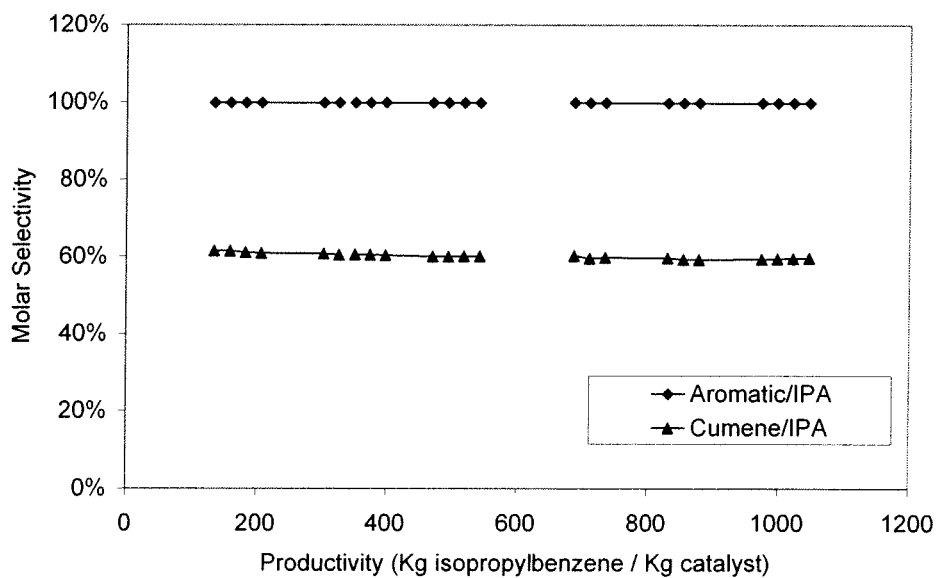

The same reactor setup described in Example 2, was used in this example. Thirty grams of MCM-22, catalyst was loaded into the fixed bed reactor. A feed comprised of 79.2, wt % benzene and 20.8, wt % isopropanol, equivalent to benzene to isopropanol molar ratio of 2.9:1,, was fed to the reactor at 74, grams per hour, giving an isopropanol WHSV of 0.5, $hr^-$, . The reactor circulation was adjusted to give a moisture content of 9,800, ppm in the reactor. The inlet temperature was 230° C., the reactor pressure was maintained at 470, psig (3342 kPa), and the reaction took place in complete liquid phase. The propylene and isopropanol conversions were both 100% throughout the run. As shown in FIG. 12, the catalyst performance was stable after the minor initial change and no aging as shown in the Examples of U.S. Pat. No. 6,512,153, was observed.

EXAMPLE 13

Figure 13:
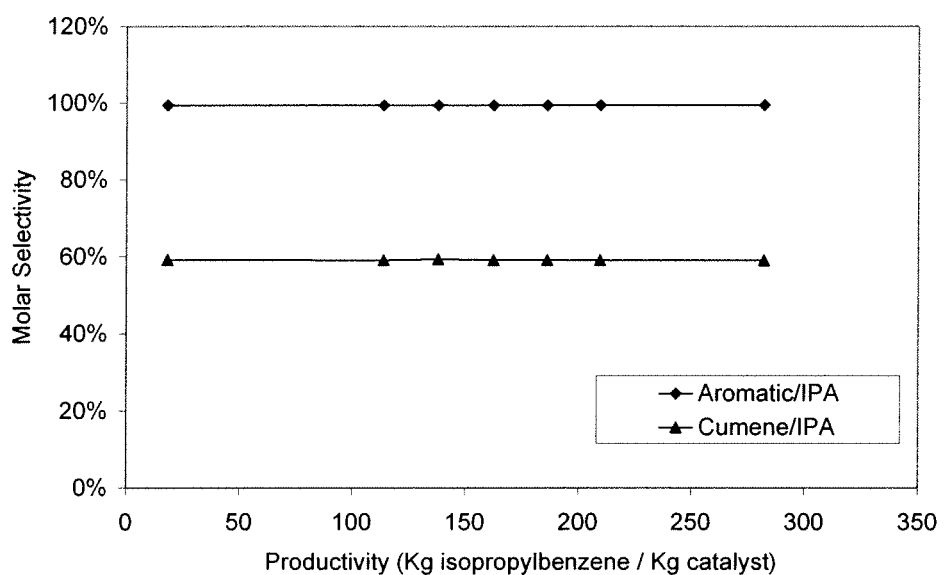

The same reactor setup and catalyst loading described in Example 12 were used in this example. A feed comprised of 79.2, wt % benzene and 20.8, wt % isopropanol, equivalent to a benzene to isopropanol molar ratio of 2.9:1,, was fed to the reactor at 73, grams per hour, giving an isopropanol WHSV of 0.5, $hr^{-1}$. The reactor circulation was adjusted to give a moisture content of 15,800, ppm in the reactor. The inlet temperature was 250° C., the reactor pressure was maintained at 550, psig (3893, kPa), and the reaction took place in mixed gas-liquid phase. The moisture content in the liquid phase was calculated to be 13,400, ppm. The isopropanol conversion was 100% throughout the run. The Cumene/Isopropanol selectivity observed in this example was essentially the same as that observed in example 12. As shown in FIG. 13, the catalyst performance was stable throughout the run and no aging as shown in the Examples of U.S. Pat. No. 6,512,153.

EXAMPLE 14

Figure 14:
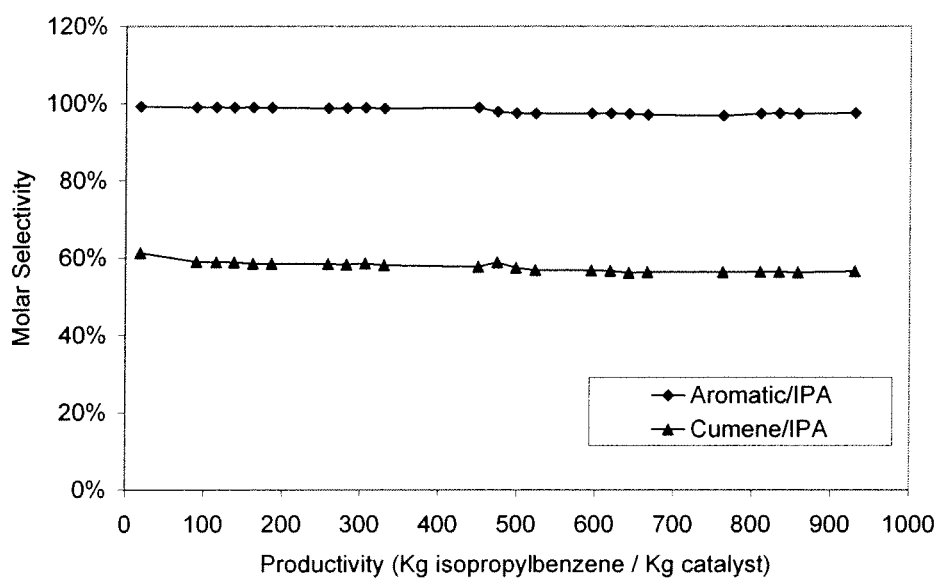

The same reactor setup and catalyst loading described in Example 13 were used in this example. A feed comprised of 72.2, wt % benzene and 27.8, wt % isopropanol, equivalent to a benzene to isopropanol molar ratio of 2.0:1,, was fed to the reactor at 57, grams per hour, giving an isopropanol WHSV of 0.5, $hr^{-1}$. The reactor circulation was adjusted to give a moisture content of 15,600, ppm in the reactor. The inlet temperature was 250° C., the reactor pressure was maintained at 550, psig (3893, kPa), and the reaction took place in mixed gas-liquid phase. The moisture content in the liquid phase was calculated to be 14,900, ppm. The isopropanol conversion was 100% throughout the run. As shown in FIG. 14, the catalyst performance was stable throughout the run and no aging as shown in the Examples of U.S. Pat. No. 6,512,153.

EXAMPLE 15

Figure 15:
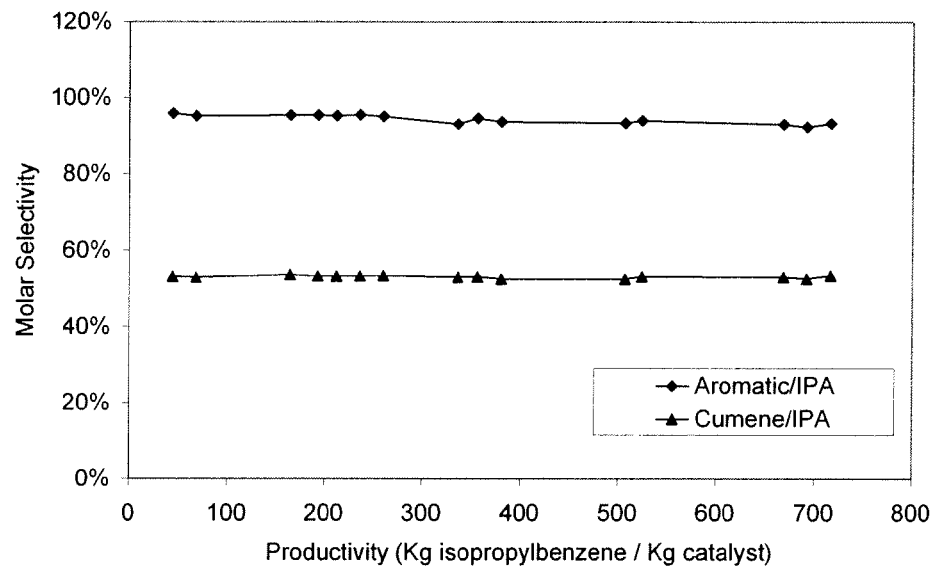

The same reactor setup and catalyst loading described in Example 14 were used in this example. A feed comprised of 72.2, wt % benzene and 27.8, wt % isopropanol, equivalent to a benzene to isopropanol molar ratio of 2.0:1,, was fed to the reactor at 56, grams per hour, giving an isopropanol WHSV of 0.5, $hr^{-1}$. The reactor circulation was adjusted to give a moisture content of 5,200, ppm in the reactor. The inlet temperature was 210° C., the reactor pressure was maintained at 550, psig (3893, kPa), and the reaction took place in complete liquid phase. The isopropanol conversion was 100% throughout the run. As shown in FIG. 15, the catalyst performance was stable throughout the run.

EXAMPLE 16

Figure 16:
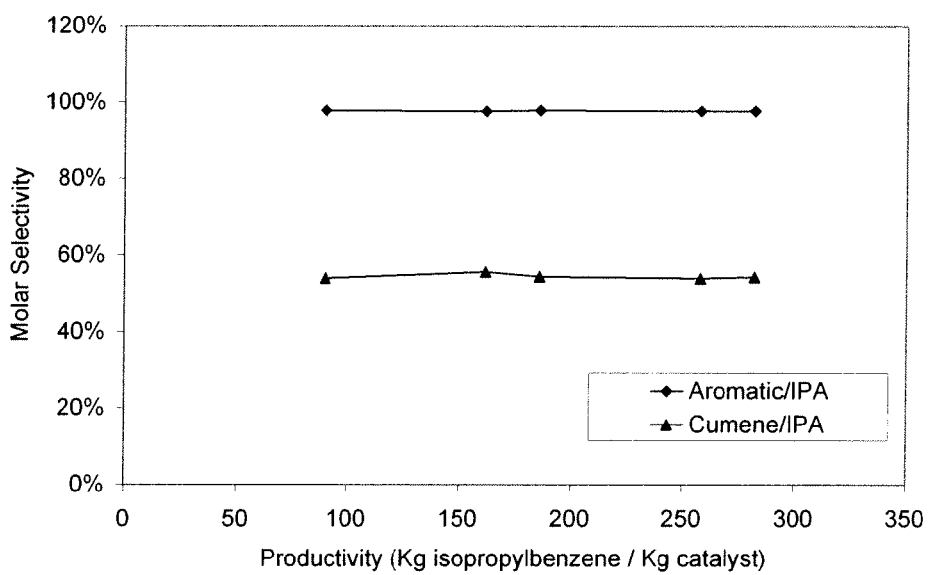

The same reactor setup and catalyst loading described in Example 15 were used in this example. A feed comprised of 72.2, wt % benzene and 27.8, wt % isopropanol, equivalent to a benzene to isopropanol molar ratio of 2.0:1,, was fed to the reactor at 58, grams per hour, giving an isopropanol WHSV of 0.5, $hr^{-1}$. The reactor circulation was adjusted to give a moisture content of 5,100, ppm in the reactor. The inlet temperature was 230° C., the reactor pressure was maintained at 550, psig (3893, kPa), and the reaction took place in complete liquid phase. The isopropanol conversion was 100% throughout the run. As shown in FIG. 16, the catalyst performance was stable throughout the run.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cumene comprising contacting a feed stream comprising benzene and a further feed stream comprising isopropanol or a mixture of isopropanol and propylene in the presence of an alkylation catalyst comprising at least a molecular sieve of the MCM-22, family in an alkylation zone under alkylation conditions of at least partial liquid phase and with a water concentration in the liquid phase of at least 50 ppm to react at least part of said isopropanol and benzene to produce an effluent stream containing cumene.

2. The process of claim 1 wherein said molecular sieve of the MCM-22, family has an X-ray diffraction pattern including d-spacing maxima at 12.4±0.25, 6.9±0.15, 3.57±0.07 and 3.42±0.07 Angstroms.

3. The process of claim 1 wherein said molecular sieve of the MCM-22, family is selected from MCM-22, PSH-3, SSZ-25, ERB-1, ITQ-1, ITQ-2, MCM-36, MCM-49, MCM-56, UZM-8, and mixtures thereof.

4. The process of claim 1 wherein said alkylation catalyst further comprises at least one zeolite catalyst selected from the group comprising ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Dealuminized Y (Deal Y), mordenite, MCM-22, PSH-3, SSZ-25, ERB-1, ITQ-1, ITQ-2, MCM-36, MCM-49, MCM-56, and UZM-8.

5. The process of claim 1 wherein the concentration of water in the liquid phase is at least 100 ppm.

6. The process of claim 1 wherein the concentration of water in the liquid phase is no more than 40,000 ppm.

7. The process of claim 1 wherein the concentration of water in the liquid phase ranges between 8,500 and 40,000 ppm.

8. The process of claim 1 wherein said alkylation conditions further comprise a temperature of 20° C. to 350° C., a pressure of 100 kPa to 20,000 kPa, and a molar ratio of benzene to $C_3$ alkylating agent (isopropanol plus any propylene) fed to said alkylation zone 0.1:1; to 100:1.

9. The process of claim 8 wherein the molar ratio of benzene to $C_3$ alkylating agent (isopropanol plus any propylene) fed to said alkylation zone ranges between 0.3:1 to 10:1.

10. The process of claim 8 wherein the temperature ranges between 100 to 300° C.

11. The process of claim 1 wherein said further feed stream comprises a mixture of isopropanol and propylene and the isopropanol to propylene molar ratio in the mixture ranges from 99.9:0.1 and 0.1:99.9.

12. The process of claim 1 and further comprising recycling at least part of said effluent stream to said alkylation zone.

13. The process of claim 1 and further comprising:
(i) cooling the said effluent stream;
(ii) separating said cooled effluent stream into a water-rich aqueous stream and an aromatic stream composed mainly of cumene and unreacted benzene; and
(iii) recycling at least part of said aromatic stream to the alkylation zone.

14. An integrated process for producing phenol, the process comprising:
(a) contacting a feed stream comprising benzene and a further feed stream comprising isopropanol or a mixture of isopropanol and propylene in the presence of an alkylation catalyst comprising at least a molecular sieve of the MCM-22, family in an alkylation zone under alkylation conditions of at least partial liquid phase and with a water concentration in the liquid phase of at least 50 ppm to react at least part of said isopropanol and benzene to produce an effluent stream containing cumene;
(b) oxidizing at least part of the cumene produced in (a) to form cumene hydroperoxide;
(c) cleaving at least part of the cumene hydroperoxide from (b) to form a cleavage effluent stream containing phenol and acetone;
(d) separating at least part of the acetone from the cleavage effluent stream;
(e) hydrogenating at least part of the acetone separated in (d) to produce isopropanol; and
(f) recycling at least part of the isopropanol produced in (e) to said contacting (a).

15. The process of claim 14 wherein said molecular sieve of the MCM-22, family has an X-ray diffraction pattern including d-spacing maxima at 12.4±0.25, 6.9±0.15, 3.57±0.07 and 3.42±0.07 Angstroms.

16. The process of claim 14 wherein said molecular sieve of the MCM-22, family is selected from MCM-22, PSH-3, SSZ-25, ERB-1, ITQ-1, ITQ-2, MCM-36, MCM-49, MCM-56, UZM-8, and mixtures thereof.

17. The process of claim 1 wherein the concentration of water in the liquid phase is at least 500 ppm.

18. The process of claim 1 wherein the concentration of water in the liquid phase is at least 1,000 ppm.

19. The process of claim 1 wherein the concentration of water in the liquid phase ranges between 8,500 and 20,000 ppm.

20. The process of claim 8 wherein the molar ratio of benzene to $C_3$ alkylating agent (isopropanol plus any propylene) fed to said alkylation zone ranges between 0.5:1 to 5:1.

21. The process of claim 8 wherein the molar ratio of benzene to $C_3$ alkylating agent (isopropanol plus any propylene) fed to said alkylation zone ranges between 1:1 to 3:1.

22. The process of claim 8 wherein the temperature ranges between 150 to 280° C.

\* \* \* \* \*

UNITED STATES PATENT AND TRADEMARK OFFICE
CERTIFICATE OF CORRECTION

PATENT NO. : 8,445,738 B2
APPLICATION NO. : 13/119781
DATED : May 21, 2013
INVENTOR(S) : Hwang et al.

Page 1 of 1

It is certified that error appears in the above-identified patent and that said Letters Patent is hereby corrected as shown below:

On the Title page, Item [57] in Line 5 of the Abstract delete "," after "MCM-22"

In the Specification

In Col. 4, Line 26 delete "," after "MCM-22"

In Col. 5, Lines 11, 56, 57, 58 and 59 delete "," after "MCM-22"

In Col. 6, Lines 17, 25, 35 and 49 delete "," after "MCM-22"

In Col. 7, Line 52 delete "," after "MCM-22"

In Col. 8, Line 43 delete "," after "MCM-22"

In the Claims:

In Col. 13, Claim 1, Line 37 and Col. 13, Claim 2, Line 43 delete "," after "MCM-22"

In Col. 13, Claim 3, Line 47 delete "," after first "MCM-22"

In Col. 14, Claim 14, Line 29 and Claim 15, Line 47 delete "," after "MCM-22"

In Col. 14, Claim 15, Line 51 delete "," after first "MCM-22"

Signed and Sealed this
Twenty-fourth Day of September, 2013

Teresa Stanek Rea
*Deputy Director of the United States Patent and Trademark Office*